US006440688B1

(12) United States Patent
Bruce et al.

(10) Patent No.: US 6,440,688 B1
(45) Date of Patent: Aug. 27, 2002

(54) ENZYMATIC COFACTOR CYCLING USING SOLUBLE PYRIDINE NUCLEOTIDE TRANSHYDROGENASE

(75) Inventors: Neil Charles Bruce; Christopher Edward French, both of Cambridge (GB)

(73) Assignee: Cambridge University Technical Services Limited (GB)

( * ) Notice: Subject to any disclaimer, the term of this patent is extended or adjusted under 35 U.S.C. 154(b) by 0 days.

(21) Appl. No.: 09/297,468

(22) PCT Filed: Oct. 29, 1997

(86) PCT No.: PCT/GB97/02983

§ 371 (c)(1),
(2), (4) Date: Jul. 12, 1999

(87) PCT Pub. No.: WO98/18909

PCT Pub. Date: May 7, 1998

(30) Foreign Application Priority Data

Oct. 29, 1996 (GB) .............................................. 9622516

(51) Int. Cl.$^7$ ............................. C12Q 1/32; C12N 9/04; C12N 15/00; C12N 1/20; C07H 21/04
(52) U.S. Cl. ...................... 435/26; 435/190; 435/320.1; 435/252.3; 435/252.33; 435/41; 536/23.2
(58) Field of Search ........................ 435/252.3, 252.33, 435/190, 320.1, 26, 41; 536/23.2

(56) References Cited

FOREIGN PATENT DOCUMENTS

| EP | 0388267 | 9/1990 |
| EP | 0733712 | 9/1996 |
| WO | 9013634 | 11/1990 |

OTHER PUBLICATIONS

Dorland's Medical Dictionary, 27th edition, p. 209, 1988.*
Wermuth, B. et al. (1976) "Pyridine Nucleotide Transhydrogenase From Pseudomonas Aeruginosa: Purification by Affinity Chromatography and Physicochemical Properties" Archives of Biochemistry and Biophysics 176(1):136–143.
Clarke, D. M. et al. (1986) "Nucleotide Sequence of the PNT A and PNT B Genes Encoding the Pyridine Nucleotide Transhydrogenase of *Escherichia Coli*" European Journal of Biochemistry 158(3):647–653.
Bruce, N. C. et al. (1994) "Towards engineering pathways for the synthesis of analgesics and antitussives" Annals of the New York Academy of Sciences 721:85–99.

French, C. E. et al. (1997) "Cloning sequencing, and properties of the soluble pyridine nucleotide transhydrogenase of Pseudomonas fluorescens" Journal of Bacteriology 179(8):2761–2765.

* cited by examiner

*Primary Examiner*—Rebecca E. Prouty
*Assistant Examiner*—Maryam Monshipouri
(74) *Attorney, Agent, or Firm*—Salinwanchik, Lloyd & Saliwanchik (57) ABSTRACT

The present invention pertains to an enzymatic reaction involving a pyridine nucleotide cofactor, wherein an enzyme is used that has a sequence of greater than 70% identity to SEQ ID NO: 2 and is capable of transferring reducing equivalents between pyridine nucleotide cofactors. Alternatively, a cell transformed to express the enzyme may be used.

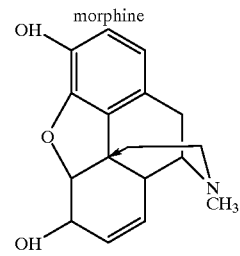

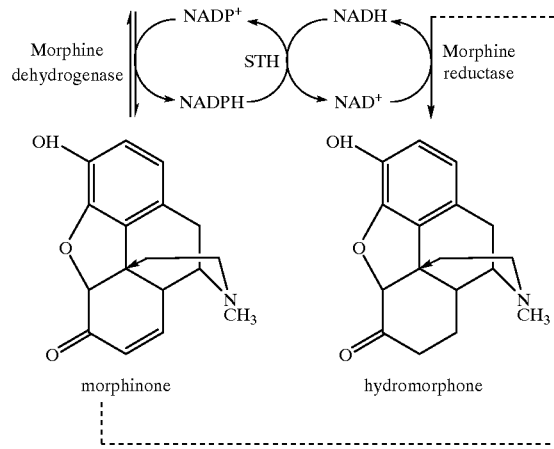

11 Claims, 5 Drawing Sheets

*E. coli* JM109/pMORB3-AmutMC80S/pPNT4

*E. coli* JM109/pMORB3-AmutMC80S

FIGURE 4

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1660 base pairs
      (B) TYPE: nucleic acid
      (C) STRANDEDNESS: double
      (D) TOPOLOGY: linear    (ii) MOLECULE TYPE: DNA (genomic)

(iii) HYPOTHETICAL: NO

(iv) ANTI-SENSE: NO

(ix) FEATURE:
      (A) NAME/KEY: CDS
      (B) LOCATION:209..1600

(xi) SEQUENCE DESCRIPTION: SEQ ID NO: 1:

```
ACGGGCGGTG AAACGTAACG AGTGCTGTGT AGTAAAGGCA AAACTGGCTA CGGAACGCGA        60

CCAAGGGTTA ATGTGCGCGG CGTTGAGCCT TATATAGACT GTGCCCCGGT TCAACACACT       120

TGAGCCAAAT TGTCCTTCAT GACCGCTGGC CGCGGCATGA TTTAGCCAGG CGTCCAACCG       180

TACGCCTGGC CTGTTTTGAG GAGTACGC ATG GCT GTC TAC AAC TAC GAC GTG         232
                                Met Ala Val Tyr Asn Tyr Asp Val
                                  1               5

GTG GTA CTG GGT TCC GGC CCG GCT GGA GAA GGT GCG GCG ATG AAC GCC         280
Val Val Leu Gly Ser Gly Pro Ala Gly Glu Gly Ala Ala Met Asn Ala
     10              15                  20

GCG AAG GCA GGG CGC AAG GTG GCG ATG GTC GAT AGC CGT CGC CAG GTC         328
Ala Lys Ala Gly Arg Lys Val Ala Met Val Asp Ser Arg Arg Gln Val
 25              30                  35                      40

GGC GGT AAC TGC ACC CAC CTG GGT ACC ATC CCG TCC AAG GCA TTG CGT         376
Gly Gly Asn Cys Thr His Leu Gly Thr Ile Pro Ser Lys Ala Leu Arg
                 45                  50                  55

CAC TCC GTT CGC CAG ATC ATG CAG TTC AAC ACC AAC CCG ATG TTC CGG         424
His Ser Val Arg Gln Ile Met Gln Phe Asn Thr Asn Pro Met Phe Arg
             60                  65                  70

GCC ATT GGC GAG CCG CGC TGG TTC TCG TTC CCG GAT GTG TTG AAA AGC         472
Ala Ile Gly Glu Pro Arg Trp Phe Ser Phe Pro Asp Val Leu Lys Ser
```

-continued

```
                         75                    80                      85
GCT GAA AAA GTC ATC TCC AAG CAA GTC GCC TCG CGT ACC GGC TAC TAC       520
Ala Glu Lys Val Ile Ser Lys Gln Val Ala Ser Arg Thr Gly Tyr Tyr
     90                      95                    100

GCC CGT AAC CGC GTC GAC CTG TTC TTC GGT ACC GGC AGC TTC GCC GAC       568
Ala Arg Asn Arg Val Asp Leu Phe Phe Gly Thr Gly Ser Phe Ala Asp
105                     110                     115                     120

GAG CAA ACC GTC GAG GTG GTC TGC GCC AAT GGC GTG GTC GAG AAA CTG       616
Glu Gln Thr Val Glu Val Val Cys Ala Asn Gly Val Val Glu Lys Leu
                    125                     130                     135

GTG GCC AAG CAC ATC ATC ATT GCC ACC GGC TCG CGC CCG TAT CGC CCG       664
Val Ala Lys His Ile Ile Ile Ala Thr Gly Ser Arg Pro Tyr Arg Pro
                140                     145                     150

GCG GAT ATC GAT TTC CAC CAC CCA CGT ATC TAC GAT AGC GAT ACC ATC       712
Ala Asp Ile Asp Phe His His Pro Arg Ile Tyr Asp Ser Asp Thr Ile
            155                     160                     165

CTC AGC CTG GGC CAC ACC CCA CGC AAA CTG ATC ATC TAT GGC GCC GGC       760
Leu Ser Leu Gly His Thr Pro Arg Lys Leu Ile Ile Tyr Gly Ala Gly
        170                     175                     180

GTC ATT GGC TGT GAA TAC GCC TCG ATC TTC AGC GGC CTG GGT GTG CTG       808
Val Ile Gly Cys Glu Tyr Ala Ser Ile Phe Ser Gly Leu Gly Val Leu
185                     190                     195                     200

GTC GAG CTG GTC GAC AAC CGC GAC CAG TTG CTG AGC TTC CTC GAC TCG       856
Val Glu Leu Val Asp Asn Arg Asp Gln Leu Leu Ser Phe Leu Asp Ser
                    205                     210                     215

GAA ATC TCC CAG GCG TTG AGC TAC CAC TTC AGC AAC AAC AAC ATC ACT       904
Glu Ile Ser Gln Ala Leu Ser Tyr His Phe Ser Asn Asn Asn Ile Thr
                220                     225                     230

GTG CGC CAT AAC GAA GAG TAC GAT CGG GTC GAA GGC CTG GAC AAC GGG       952
Val Arg His Asn Glu Glu Tyr Asp Arg Val Glu Gly Leu Asp Asn Gly
            235                     240                     245

GTG ATC CTG CAC CTC AAG TCC GGC AAG AAG ATC AAG GCC GAC GCC TTG      1000
Val Ile Leu His Leu Lys Ser Gly Lys Lys Ile Lys Ala Asp Ala Leu
        250                     255                     260

CTG TGG TGC AAC GGT CGT ACC GGC AAC ACC GAC AAG CTG GGC ATG GAA      1048
Leu Trp Cys Asn Gly Arg Thr Gly Asn Thr Asp Lys Leu Gly Met Glu
265                     270                     275                     280

AAC ATC GGG GTC AAG GTC AAC AGC CGT GGC CAG ATC GAG GTG GAC GAA      1096
Asn Ile Gly Val Lys Val Asn Ser Arg Gly Gln Ile Glu Val Asp Glu
                    285                     290                     295

AAC TAC CGC ACC TGT GTG ACC AAC ATC TAT GGC GCC GGT GAC GTG ATC      1144
Asn Tyr Arg Thr Cys Val Thr Asn Ile Tyr Gly Ala Gly Asp Val Ile
                300                     305                     310

GGC TGG CCG AGC CTG GCC AGT GCC GCC CAT GAC CAG GGC CGT TCG GCC      1192
Gly Trp Pro Ser Leu Ala Ser Ala Ala His Asp Gln Gly Arg Ser Ala
            315                     320                     325

GCT GGC AGC ATC GTC GAC AAC GGC AGC TGG CGC TAT GTG AAC GAC GTA      1240
Ala Gly Ser Ile Val Asp Asn Gly Ser Trp Arg Tyr Val Asn Asp Val
        330                     335                     340

CCG ACC GGG ATC TAC ACG ATT CCG GAG ATC AGC TCG ATC GGC AAG AAC      1288
Pro Thr Gly Ile Tyr Thr Ile Pro Glu Ile Ser Ser Ile Gly Lys Asn
345                     350                     355                     360

GAA CAC GAA CTG ACC AAG GCC AAG GTG CCT TAC GAA GTG GGC AAG GCG      1336
Glu His Glu Leu Thr Lys Ala Lys Val Pro Tyr Glu Val Gly Lys Ala
                    365                     370                     375

TTC TTC AAG AGC ATG GCG CGT GCG CAG ATC GCC GGT GAG CCG CAA GGC      1384
Phe Phe Lys Ser Met Ala Arg Ala Gln Ile Ala Gly Glu Pro Gln Gly
                380                     385                     390

ATG CTG AAG ATC CTG TTT CAC CGC GAG ACC CTG GAA GTC CTC GGC GTG      1432
```

```
Met Leu Lys Ile Leu Phe His Arg Glu Thr Leu Glu Val Leu Gly Val
        395                 400                 405

CAT TGC TTC GGC TAC CAG GCT TCG GAG ATC GTG CAC ATC GGC CAG GCC        1480
His Cys Phe Gly Tyr Gln Ala Ser Glu Ile Val His Ile Gly Gln Ala
410                 415                 420

ATC ATG AAC CAG CCG GGC GAG CAA AAT ACC CTC AAG TAT TTC GTC AAC        1528
Ile Met Asn Gln Pro Gly Glu Gln Asn Thr Leu Lys Tyr Phe Val Asn
425                 430                 435                 440

ACC ACC TTC AAC TAC CCG ACC ATG GCC GAA GCC TAT CGG GTA GCG GCC        1576
Thr Thr Phe Asn Tyr Pro Thr Met Ala Glu Ala Tyr Arg Val Ala Ala
            445                 450                 455

TAC GAT GGC CTC AAC CGG CTT TTT TGAGCGGCTC CGGCCGGTGG CCTGAGCCGG       1630
Tyr Asp Gly Leu Asn Arg Leu Phe
                460

CCGGGGAGAC CGATTTCAGT AATTCTCGAG                                       1660

(2) INFORMATION FOR SEQ ID NO: 2:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Val Tyr Asn Tyr Asp Val Val Leu Gly Ser Gly Pro Ala
 1               5                  10                  15

Gly Glu Gly Ala Ala Met Asn Ala Ala Lys Ala Gly Arg Lys Val Ala
                20                  25                  30

Met Val Asp Ser Arg Arg Gln Val Gly Gly Asn Cys Thr His Leu Gly
            35                  40                  45

Thr Ile Pro Ser Lys Ala Leu Arg His Ser Val Arg Gln Ile Met Gln
        50                  55                  60

Phe Asn Thr Asn Pro Met Phe Arg Ala Ile Gly Glu Pro Arg Trp Phe
65                  70                  75                  80

Ser Phe Pro Asp Val Leu Lys Ser Ala Glu Lys Val Ile Ser Lys Gln
                85                  90                  95

Val Ala Ser Arg Thr Gly Tyr Tyr Ala Arg Asn Arg Val Asp Leu Phe
                100                 105                 110

Phe Gly Thr Gly Ser Phe Ala Asp Glu Gln Thr Val Glu Val Val Cys
            115                 120                 125

Ala Asn Gly Val Val Glu Lys Leu Val Ala Lys His Ile Ile Ile Ala
130                 135                 140

Thr Gly Ser Arg Pro Tyr Arg Pro Ala Asp Ile Asp Phe His His Pro
145                 150                 155                 160

Arg Ile Tyr Asp Ser Asp Thr Ile Leu Ser Leu Gly His Thr Pro Arg
                165                 170                 175

Lys Leu Ile Ile Tyr Gly Ala Gly Val Ile Gly Cys Glu Tyr Ala Ser
                180                 185                 190

Ile Phe Ser Gly Leu Gly Val Leu Val Glu Leu Val Asp Asn Arg Asp
            195                 200                 205

Gln Leu Leu Ser Phe Leu Asp Ser Glu Ile Ser Gln Ala Leu Ser Tyr
        210                 215                 220

His Phe Ser Asn Asn Ile Thr Val Arg His Asn Glu Glu Tyr Asp
225                 230                 235                 240

Arg Val Glu Gly Leu Asp Asn Gly Val Ile Leu His Leu Lys Ser Gly
```

-continued

```
                    245                     250                     255
Lys Lys Ile Lys Ala Asp Ala Leu Leu Trp Cys Asn Gly Arg Thr Gly
            260                 265                 270

Asn Thr Asp Lys Leu Gly Met Glu Asn Ile Gly Val Lys Val Asn Ser
        275                 280                 285

Arg Gly Gln Ile Glu Val Asp Glu Asn Tyr Arg Thr Cys Val Thr Asn
        290                 295                 300

Ile Tyr Gly Ala Gly Asp Val Ile Gly Trp Pro Ser Leu Ala Ser Ala
305                 310                 315                 320

Ala His Asp Gln Gly Arg Ser Ala Ala Gly Ser Ile Val Asp Asn Gly
                325                 330                 335

Ser Trp Arg Tyr Val Asn Asp Val Pro Thr Gly Ile Tyr Thr Ile Pro
            340                 345                 350

Glu Ile Ser Ser Ile Gly Lys Asn Glu His Glu Leu Thr Lys Ala Lys
            355                 360                 365

Val Pro Tyr Glu Val Gly Lys Ala Phe Phe Lys Ser Met Ala Arg Ala
        370                 375                 380

Gln Ile Ala Gly Glu Pro Gln Gly Met Leu Lys Ile Leu Phe His Arg
385                 390                 395                 400

Glu Thr Leu Glu Val Leu Gly Val His Cys Phe Gly Tyr Gln Ala Ser
                405                 410                 415

Glu Ile Val His Ile Gly Gln Ala Ile Met Asn Gln Pro Gly Glu Gln
            420                 425                 430

Asn Thr Leu Lys Tyr Phe Val Asn Thr Thr Phe Asn Tyr Pro Thr Met
            435                 440                 445

Ala Glu Ala Tyr Arg Val Ala Ala Tyr Asp Gly Leu Asn Arg Leu Phe
450                 455                 460
```

ENZYMATIC COFACTOR CYCLING USING SOLUBLE PYRIDINE NUCLEOTIDE TRANSHYDROGENASE

FIELD OF THE INVENTION

This invention relates to the use of an enzyme for the oxidation or reduction of pyridine nucleotide cofactors during enzymic reactions in vivo or in vitro, for example in enzymic or whole-cell biotransformations or enzymic analytical techniques.

BACKGROUND OF THE INVENTION

Biotransformation procedures using natural or genetically-modified microorganisms or isolated enzymes provide methods for the synthesis of many useful products. Biotransformations have several advantages over chemical synthetic methods, in particular regiospecificity and stereospecificity of the enzyme-catalysed reactions, use of mild reaction conditions, and absence of requirement for toxic solvents.

Oxidoreductase enzymes often require redox-active cofactors for activity. Among the most common such cofactors are the pyridine nucleotide cofactors nicotinamide adenine dinucleotide (NAD: oxidized form $NAD^+$, reduced form NADH) and nicotinamide adenine dinucleotide phosphate (NADP: oxidized form $NADP^+$, reduced form NADPH). These cofactors are expensive and, except in the cases of extremely valuable products, cannot feasibly be supplied in stoichiometric quantities. This is one factor limiting the use of many oxidoreductase enzymes for biotransformation reactions.

The requirement for cofactors in a biotransformation process can be reduced by the provision of a means of regenerating the desired form of the cofactor. This means that the cofactor need be supplied only in catalytic quantities. For example, if the reaction of interest requires $NAD^+$, which is reduced in the reaction to NADH, the NADH can be re-oxidized by $NAD^+$ by another enzyme system, such as $NAD^+$-dependent formic dehydrogenase in the presence of formate. This is referred to as cofactor cycling. Formic dehydrogenase is particularly suitable for this purpose, since the reaction it catalyses is essentially irreversible.

A further complication is that the majority of NAD-requiring enzymes are not able to use NADP as a cofactor, and vice versa. For example, formic dehydrogenase could not be used to regenerate NADPH from $NADP^+$.

Figure 1A:
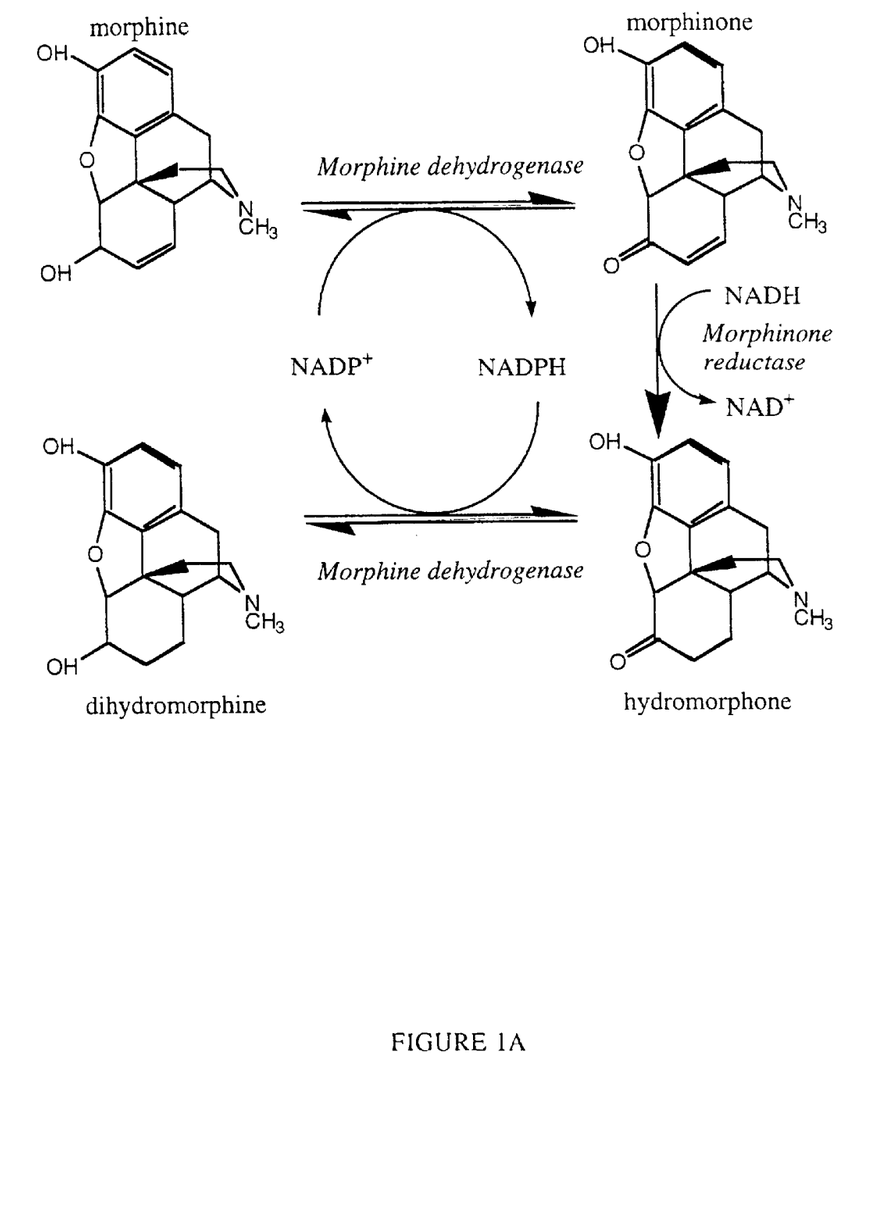

A special case is where a biotransformation process requires two oxidoreductase enzymes which require different cofactors. For example, a recently proposed biotransformation process for the conversion of morphine to the powerful painkiller hydromorphone requires the sequential action of $NADP^+$-dependent morphine dehydrogenase and NADH-dependent morphinone reductase (French et al (1995) Bio/Technology 13:674–676). In the first reaction, morphine is converted to morphinone with reduction of $NADP^+$ to NADPH, and in the second reaction morphinone is converted to hydromorphone with oxidation of NADH to $NAD^+$. Therefore, both $NADP^+$ and NADH must be supplied. A further complication is that, in the presence of NADPH generated in the first reaction, morphine dehydrogenase reduces the product hydromorphone to an undesirable product, dihydromorphine, with re-oxidation of NADPH to $NADP^+$. These reactions are shown in the accompanying FIG. 1A.

Pyridine nucleotide-dependent enzymes can also be used in certain enzymic assay procedures, with the quantity of the analyte being determined by the degree of oxidation or reduction of the cofactor. Oxidation and reduction of NAD and NADP can be measured by several methods; for example, spectrophotometry and fluorimetry. However, exceptionally sensitive methods for detecting oxidation or reduction may only be available for either NAD or NADP, but not both. For example, the oxidation of NADH to $NAD^+$ can be detected with extreme sensitivity by using the enzymes glyceraldehyde-3-phosphate dehydrogenase (GAPDH) and phosphoglycerokinase (PGK) to phosphorylate adenosine diphosphate (ADP) to adenosine triphosphate (ATP) in a reaction dependent on the presence of $NAD^+$, and then detecting the resulting ATP by the ATP-dependent light-emitting reaction of firefly luciferase. This method cannot be used to detect oxidation of NADPH to $NADP^+$, since the commercially available GAPDH is specific for $NAD^+$.

Several of the problems mentioned above can be overcome by the use of an enzyme which transfers reducing equivalents between NAD and NADP; for example, reducing $NAD^+$ to NADH while oxidizing NADPH to $NADP^+$. Such an enzyme is known as a pyridine nucleotide transhydrogenase (PNTH). Several types of enzyme exhibit this activity (Rydström et al (1987) in 'Pyridine nucleotide coenzymes: chemical, biochemical and medical aspects', part B, eds. Dolphin et al, John Wiley and Sons, NY, p.433–460) The best known is the membrane-bound, proton-pumping, PNTH found in the membranes of mitochondria and certain bacteria such as *Escherichia coli*. This enzyme, being membrane-bound, is generally unsuitable for biotransformation and analytical purposes. Soluble, non-energy-linked PNTH has been reported to occur in certain bacteria such as *Pseudomonas fluorescens*, *Pseudomonas aeruginosa* and *Azotobacter vinelandii*. This enzyme has been characterized in some detail, but its utility is limited.

SUMMARY OF THE INVENTION

The gene (designated sth) encoding the soluble transhydrogenase of *Pseudomonas fluorescens* NCIMB 9815 has been cloned and sequenced, and the enzyme has been overexpressed in *Escherichia coli*. This enables the preparation of large amounts of enzyme relatively easily. The enzyme has been purified and characterized. This enzyme is defined by the reaction it catalyses, namely, transfer of reducing equivalents between NAD and NADP or analogues of these cofactors; the nucleotide sequence of the structural gene, sth, encoding the enzyme, and the deduced amino acid sequence of the enzyme derived therefrom; structural properties of the enzyme, including a subunit $M_r$ of approximately 50,000; and the capacity to form large polymers of $M_r$ exceeding 1,000,000.

According to a first aspect of this invention, the enzyme is used to act upon pyridine nucleotide cofactors so as to enhance a biotransformation process, for example, to alter the oxidation state of NAD or NADP or analogues of these cofactors. This may be so as to allow the action of another enzyme upon these cofactors. Alternatively, an altered form of the enzyme, prepared by random or site-directed mutagenesis of the structural gene, might be used. Such an altered enzyme may show altered levels of activity, altered regulation, or altered subunit structure.

The gene sth constitutes a second aspect of this invention. The gene may be used for the production of the enzyme or an altered form of the enzyme using a genetically modified organism. For example, a genetically modified organism carrying the sth gene as all or part of a heterologous construct may be grown in such a way as to encourage production of the enzyme, which may then be recovered from the culture medium or from cell extracts. The methods for accomplishing this are well known in the art.

A third aspect of this invention is the genetically modified organism which expresses the enzyme. Such an organism may be used in a whole cell biotransformation process which may be enhanced by the presence in the cells of the active enzyme. Techniques for generating such recombinant organisms are well known in the art.

According to a fourth aspect of the invention, the enzyme is used in enzyme-based analytical assays so as to enhance these assays. For example, the enzyme may be used to, in effect, convert a signal measured as oxidation of NADPH to $NADP^+$ to a signal that can be measured based on oxidation of NADH to $NAD^+$. The altered signal may thereafter be detected by a more sensitive technique which was not formerly applicable.

DESCRIPTION OF THE INVENTION

The invention may be utilised by the enzyme having the sequence shown in SEQ ID No.2, or an amino-acid sequence having, more than 70%, preferably at least 80%, and more preferably at least 90% identity. The enzyme may be used as such, or as a transformed organism. Suitable hosts for transformation are well known to those of ordinary skill in the art. An example of a suitable host is *E. coli*.

Figure 1B:
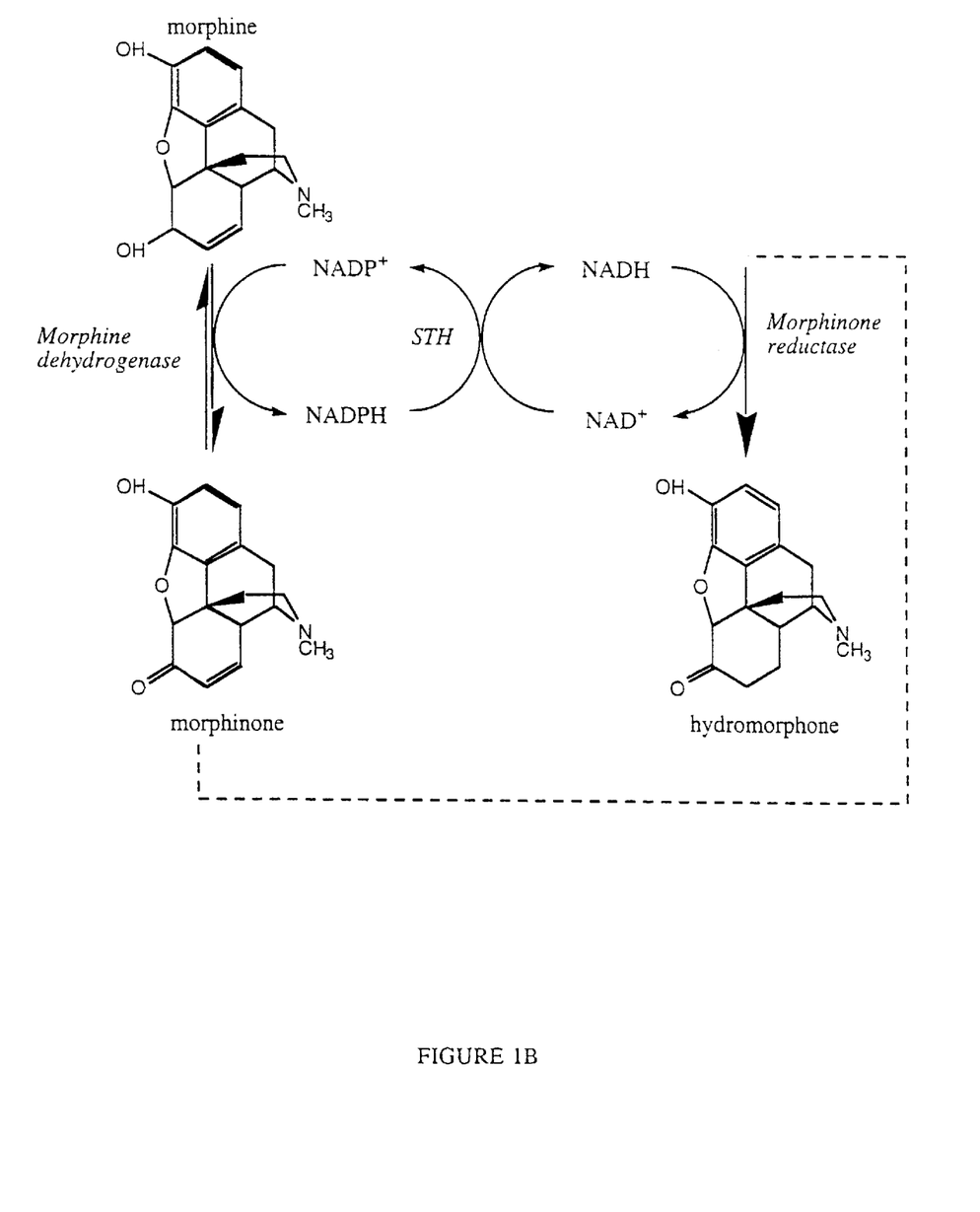

An enzyme or organism of the invention may be used in biotransformation, for analytical purposes, or for any other appropriate purpose. It is particularly useful in connection with a reaction in which an enzyme uses a pyridine nucleotide cofactor. A specific example is shown in FIG. 1B (to be compared with FIG. 1A). The use of STH means that reduction of hydromorphone is greatly decreased, by avoiding a build-up of NADH. This eliminates the need to supply expensive cofactors. In biotransformation, STH may shuttle reducing equivalents from NADH to $NAD^+$, allowing cells to be used in the process more than once.

The following Example 1 illustrates the cloning and sequencing of sth, while Examples 2 and 3 illustrate the use of STH in accordance with the invention. The Examples are given with reference to FIG. 1 (described above) and the other accompanying drawings, in which.

EXAMPLE 1

Thionicotinamide adenine dinucleotide (tNAD+) and adenosine-2',5'-diphosphate agarose were obtained from Sigma (Poole, Dorset, UK). Other reagents were of analytical or higher grade and were obtained from Sigma or Aldrich (Gillingham, Dorset, UK).

*Pseudomonas fluorescens* NCIMB9815 was obtained from the National Collection of Industrial and Marine Bacteria (Aberdeen, Scotland, UK). *Escherichia coli* JM109 was obtained from Promega (Southampton, UK). Both organisms were routinely grown in SOB medium (Sambrook et al (1989) Molecular Cloning: A Laboratory Manual, 2nd edn., Cold Spring Harbor Laboratory Press, Cold Spring Harbour, N.Y.) at 30° C. (*P. fluorescens*) or 37° C. (*E. coli*) with rotary shaking at 180 rpm.

STH activity was routinely assayed by observing the reduction of thionicotinamide adenine dinucleotide ($tNAD^+$), an analogue of $NAD^+$ with altered spectral characteristics, at 400 nm in a reaction mixture consisting of 0.1 mM $tNAD^+$ and 0.1 mM NADPH in 50 mM phosphate buffer, pH 7.0, at 30° C. One unit (U) of enzyme activity was defined as that amount of activity reducing 1 mmol of $tNAD^+$ per min under these conditions. The molar change in absorbance at 400 nm of $tNAD^+$ on reduction to tNADH was taken as 11 300 1.$mol^{-1}$ $cm^{-1}$ (Cohen et al (1970) J. Biol. Chem. 245:2825–2836). Protein concentration was routinely assayed using the reagent of Pierce (Rockford, Ill., USA) according to the manufacturer's protocol. Bovine serum albumin was used as a standard. Specific activity was calculated as units of STH activity per mg of protein (U/mg).

pBluescript SK+, a standard cloning vector, was obtained from Stratagene (Cambridge, Cambs., UK). pS 1EMBL, a low-copy number vector, is described in Poustka et al (1984) Proc. Natl. Acad. Sci. USA. 81:4129–4133. Southern blotting and DNA manipulation were performed using standard techniques (Sambrook et al, supra). Purification of STH: Soluble pyridine nucleotide transhydrogenase (STH) was purified from cells of *P. fluorescens* NCIMB9815 according to a modification of the method of Höjeberg et al (1976) Eur. J. Biochem. 66:467–475. Cells were grown to stationary phase in 1 l of SOB medium. The cells were harvested by centrifugation (5000 g, 15 min) and resuspended in 20 ml buffer A (50 mM Tris/HCl, pH 7.0, with 2 mM dithiothreitol). The cells were then disrupted by sonication (25 bursts of 5 s at 12 µm separated by 30 s pauses for cooling in an ice-water bath) using an MSE Soniprep 150. Cell debris was removed by centrifugation (25,000 g 10 min). The extract contained 93 units of STH activity at a specific activity of 0.19 U/mg.

STH was purified using a column of 1 cm inner diameter packed with 6 ml of adenosine-2',5'-diphosphate agarose (packed height 7.6 cm). The column was operated at 12 ml/h during loading and 24 ml/h during washing. All procedures were performed at 4° C. and all buffers contained 2 mM dithiothreitol. After equilibration of the column with 5 mM $CaCl_2$ in buffer A, crude extract (20 ml), to which $CaCl_2$ had been added to a final concentration of 5 mM, was loaded onto the column. The column was then washed with 90 ml of 0.4 M NaCl, 5 mM $CaCl_2$ in buffer A, followed by 24 ml of 0.7 M NaCl, 5 mM $CaCl_2$ in buffer A. Bound vice versa was eluted with 50 mM tris/HCl, pH 8.9, containing 0.4 M NaCl. Fractions of 5 ml were collected and the active fractions were pooled. The pooled product was concentrated by ultrafiltration using an Amicon 8050 ultrafiltration cell fitted with a membrane of nominal $M_r$ cutoff 10,000, and then diafiltered with buffer A to reduce the pH and salt concentration. The final volume was 1.5 ml. This material contained 62 U of STH activity at a specific activity of 140 U/mg.

This product was then applied to a gel filtration column of 1.6 cm inner diameter packed with 150 ml of Sephacryl S-300 (Pharmacia) (packed height 75 cm) equilibrated with buffer A. The column was operated at 8 ml/h. Fractions of 2 ml were collected. Active fractions (16 ml) were pooled and concentrated by ultrafiltration as described above to a final volume of 1 ml. The product contained 26 U of STH activity at a specific activity of 310 U/mg.

Prior to analysis by SDS-PAGE the sample was further concentrated by freeze-drying and resuspension in a small volume of buffer A. The reconstituted material was not active. SDS-PAGE showed a single protein band with an apparent $M_r$ of 55,000, consistent with the value reported for the enzyme from Pseudomonas aeruginosa (Rydström et al, supra). Cloning: Protein was transferred from an SDS-PAGE gel to poly(vinylidene difluoride) (PVDF) membrane (ProBlott, Applied Biosystems, Foster City, Calif., USA) using the Phast Transfer semi-dry transfer system (Pharmacia, St. Albans, Herts., UK) according to the manufacturer's instructions.

The N-terminal sequence was determined by automated Edman degradation. The N-terminal sequence of the purified PNTH was determined as:

A-V-Y-N-Y-D-V-V-V-L-G-S-(G/V)-P-A-G-E-(G/V)-A-A-M-N-A-A-(R/D)

where parentheses indicate uncertain assignments.

A codon bias table for P. fluorescens was derived based on 20 genes in the Gen-EMBL database. This revealed a significant preference for G and C in the third position for most codons. Based on this codon bias, the following degenerate oligonucleotide was designed: AC-(C/G)AC-(C/G)AC-GTC-GTA-GTT-GTA-(C/G)AC-(G/C)GC (based on residues 1 to 9 of the N-terminal sequence).

Southern blots of genomic DNA from P. fluorescens NCIMB98 5 showed that this oligonucleotide bound most strongly to a 5.0 kb Eco RI fragment. A library of Eco RI fragments of 4 to 6 kb was prepared in the cloning vector pBluescript SK+ using E. Coli JM109 as a host, and recombinant cells were screened by colony blotting using the oligonucleotide probe. Several positive colonies were isolated and all were found to bear the same 5.0 kb insert. Both orientations of the insert were recovered. The recombinant plasmids were designated pSTH1A and pSTH1B, varying only in the orientation of the Eco RI insert. The gene sth was localized by restriction mapping of the insert followed by Southern analysis using the oligonucleotide probe. Sequencing indicated the presence of an open reading frame encoding a protein of the same N-terminal sequence as that determined for STH. Various subclones were prepared in pBluescript SK+ and sequenced using vector-based primers as shown in FIG. 1. The sequence of sth and the deduced amino acid sequence of STH are shown as SEQ ID Nos. 1 and 2.

Figure 2:
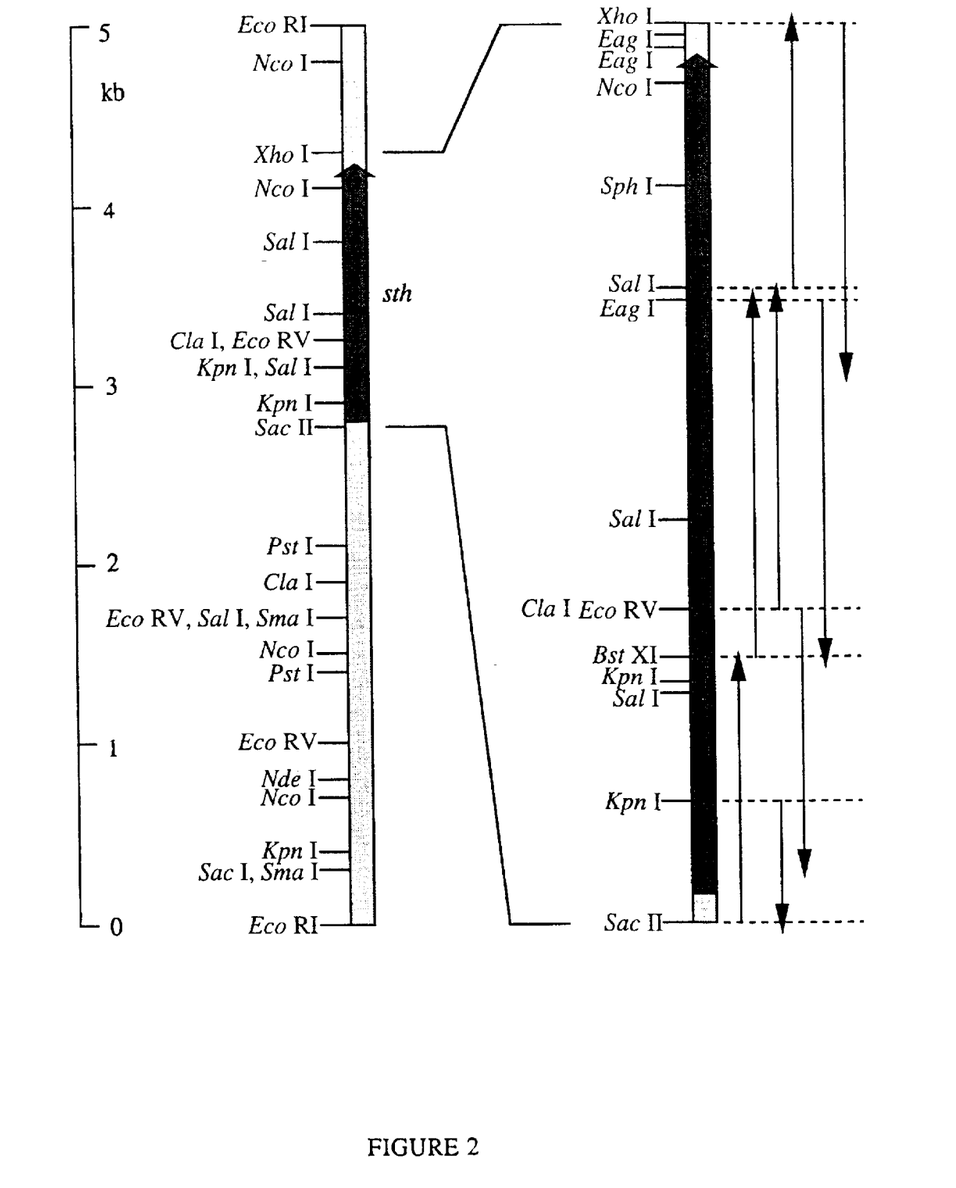
FIG. 2 is a restriction map of the 5.0 kb Eco RI fragment and the 1.5 kb Sac II/Xho I subclone bearing the sth gene. The shaded area indicates the coding region and arrows indicate sequencing reactions.

Cell extracts prepared from saturated cultures of E. coli JM109/pSTH1A or pSTH1B showed detectable STH activity, assayed by the reduction of thionicotinamide adenine dinucleotide (tNAD+) in the presence of NADPH. A 1.5 kb Sac II/Xho I fragment from pSTH1A was subcloned in pBluescript SK+ (FIG. 2). This plasmid was designated pSTH2. In pSTH2, sth is in the correct orientation to be expressed from the lac promoter of pBluescript SK+. Cell extracts from saturated cultures of E. coli JM109/pSTH2 in the absence or presence of 0.4 mM IPTG showed transhydrogenase activity of 4.1 U/mg and 22.0 U/mg respectively. Based on the specific activity of purified STH, it was estimated that in the latter case STH formed approximately 6% of soluble cell protein, approximately 100 times the level seen in P. fluorescens.

The recombinant STH was purified to apparent homogeneity in a single affinity chromatography step using adenosine-2',5'-diphosphate agarose. Cell extract was prepared as described above from 1 l of saturated culture of E. coli JM 109/pSTH2 grown in the presence of 0.4 mM IPTG. Of the resulting 25 ml of cell extract, 5 ml, containing 2140 U of STH activity at a specific activity of 27 U/mg, was loaded onto a column packed with adenosine-2',5'-diphosphate agarose a described above. The column was washed with 35 ml of 0.7 M NaCl, 5 mM $CaCl_2$ in buffer A. STH was then eluted with 0.4 M NaCl in 50 mM Tris/HCl, pH 8.9. The most active fractions, totalling 13 ml, were pooled, concentrated and diafiltered as described above, except that a membrane of nominal molecular weight cutoff 300,000 was used. The product contained 900 U of STH activity at a specific activity of 300 U/mg. This material appeared to be homogeneous by SDS-PAGE; the gel-filtration step was therefore omitted. The purified STH was stored at −20° C. in buffer A with 2 mM dithiothreitol, with no detectable loss of activity over several weeks.

The properties of the recombinant STH were compared to those reported for the enzyme from Pseudomonas aeruginosa. The subunit $M_r$ as determined by SDS-PAGE is consistent with that previously reported (Rydström et al, .supra). To determine whether the recombinant enzyme was capable of forming large polymers, samples were adsorbed to carbon films, negatively stained with 1% w/v uranyl acetate and examined by electron microscopy using a Phillips CM100 electron microscope. Long polymers of approximately 10 nm diameter and in excess of 500 nm long were observed. This is consistent with previous reports (Louie et al (1972) J. Mol. Biol. 70:651–664).

EXAMPLE 2

Morphine dehydrogenase and morphinone reductase were prepared from recombinant strains of Escherichia coli according to published procedures (Willey et al (1993) Biochem. J. 290:539–544; French and Bruce (1995) Biochem. J. 312:671–678). STH was prepared from Pseudomonas fluorescens NCIMB9815 as described in Example 1. Morphine alkaloids were quantified by HPLC (French et al, supra).

Figure 3:
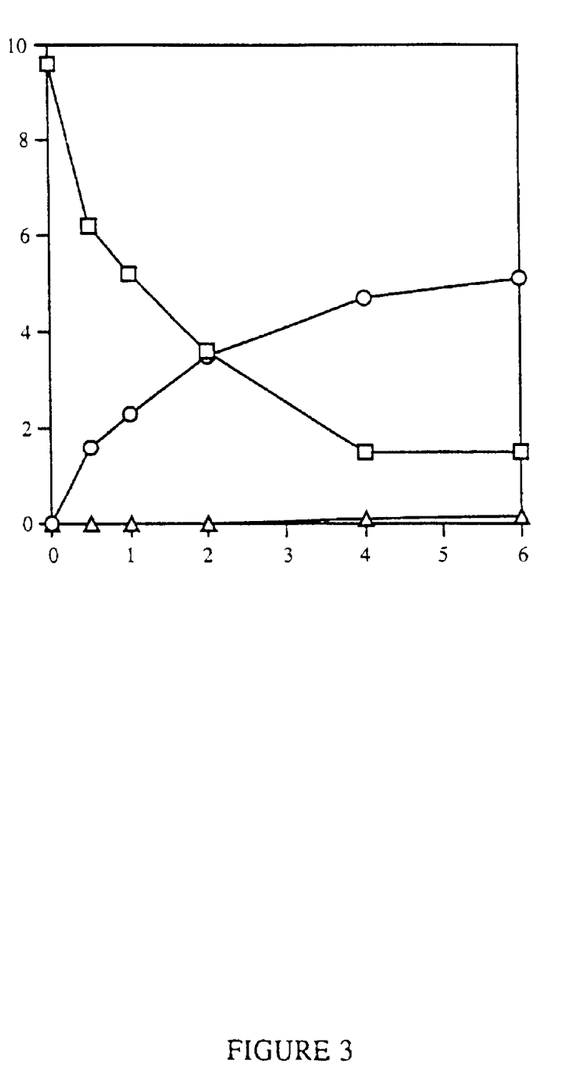
FIG. 3 shows the transformation of morphine to hydromorphone in the presence of soluble transhydrogenase. Squares, morphine; circles, hydromorphone; triangles, dihydromorphine.

A reaction mixture consisting of 0.5 ml 50 mM Tris/HCl buffer, pH 8.0, containing 10 mM morphine, 0.2 mM NADPH, 0.2 mM $NAD^+$, 1 mM dithiothreitol, 1 unit of morphinone reductase, 1 unit of morphine dehydrogenase and 6 units of STH was incubated at 4° C. for 8 hours. Samples of 50 µl were taken at intervals, treated with acetic acid to precipitate proteins, and analysed by HPLC. Morphine was converted to hydromorphone in high yield, as shown in FIG. 3. A parallel experiment lacking STH was also performed. In this case, no transformation of morphine occurred. This demonstrates that STH is capable of catalysing cycling of cofactors in an enzymic biotransformation process.

EXAMPLE 3

A 1.2 kb Pst I fragment bearing a mutant morphine dehydrogenase structural gene (morA) complete with its upstream ribosome binding site and promoter sequences was ligated into the low-copy number vector, pS 1EMBL, previously digested with Pst I creating the construct pMORA4mutMC80S, which contained suitable restriction sites for further subcloning. A 1.2 kb HindIII/Eco RI fragment carrying the mutant morA gene, ribosome binding site and promoter region was excised from pMORA4mutMC80S and ligated into HindIII/Eco RI-digested pMORB3 (French et al, supra) which carried a single copy of morB, the structural gene for morphinone reductase, together with its ribosome binding site and promoter region, creating the construct pMORB3-AmutMC80S.

A 1.5 kb Pst I/Xho I fragment bearing the structural gene for the soluble pyridine nucleotide transhydrogenase was ligated into pS 1EMBL, previously digested with Pst I and Sal I, creating the construct pPNT4.

Figure 4:
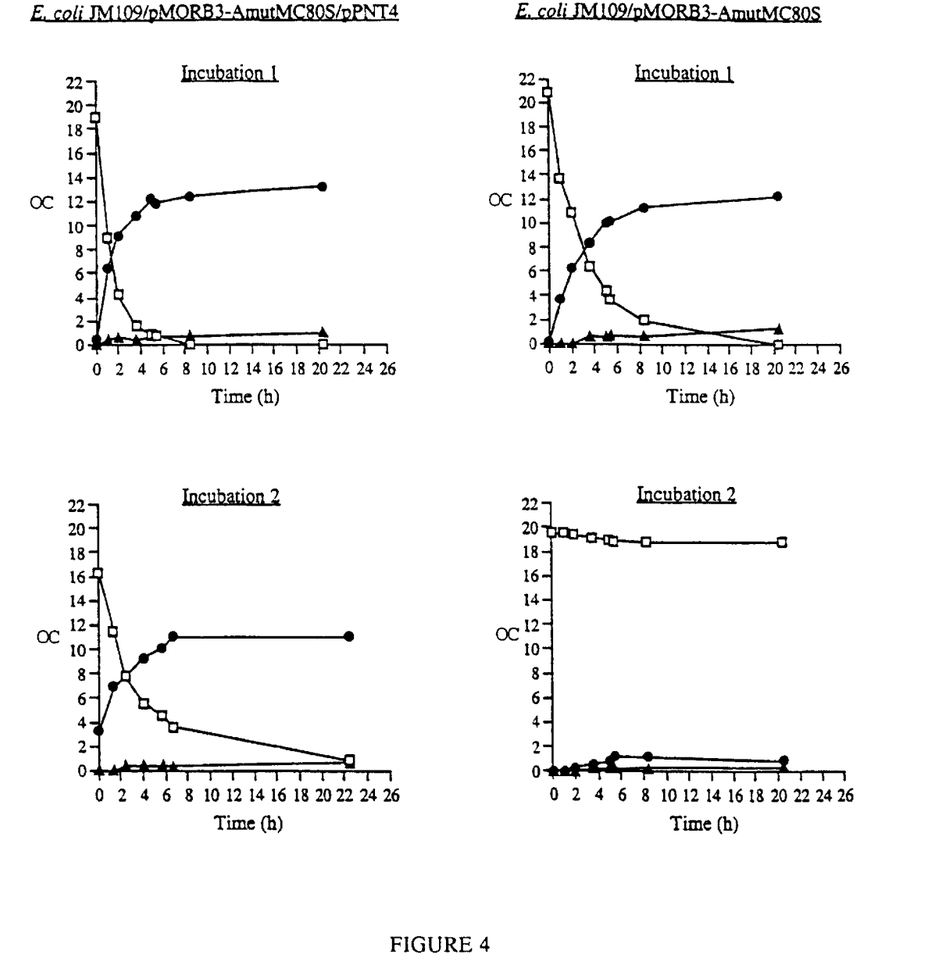
FIG. 4 shows the consecutive morphine biotransformations with cells of *E. coli* JM109/pMORB3-AmutMC80S/pPNT4 and *E. coli* JM109/pMORB3-AmutMC80S (OC= Opiate Concentration (mM), □=morphine, ●=hydromorphone and ▼=dihydromorphine).

Cells of E. coli JM109/pMORB3-AmutMC80S and E. coli JM109/pMORB3-AmutMC80S/pPNT4 were grown to stationary phase and harvested by centrifugation at 17,310×g for 15 min at 4° C. Cells were then washed with 50 mM Tris-HCl (pH 7.5) and recentrifuged. The supernatant was removed and the pelleted cells stored on ice until required for biotransformation. Typical values for enzyme activities in cells of E. coli JM109/pMORB3-AmutMC80S were 0.06 U/mg for morphine dehydrogenase and 0.88 U/mg morphinone reductase; whilst values in cells of E. coli JM109/pMORB 3-AmutMC80S/pPNT4 were 0.044 U/mg for morphine dehydrogenase, 0.78 U/mg for morphinone reductase and 0.72 U/mg for STH. Small scale whole cell biotransformations (3 ml total volume) were carried out in reaction mixtures containing 20 mM morphine and a final cell density of 0.17 g/ml in 50 mM Tris-HCl (pH 7.5). Biotransformations were carried out in duplicate at 30° C. on a rotary shaker and samples taken at regular intervals. Samples were clarified by centrifugation and analysed for opiate content using HPLC as described previously (French et al, supra). A series of consecutive biotransformations were carried out using the same batch of cells which was harvested and washed between incubations. Results illustrated in FIG. 4 indicate that cells containing recombinant STH were capable of being used more than once for the biotransformation process, while cells lacking recombinant STH could only be used once. These results imply that recombinant STH is capable of cofactor cycling in vivo enzymic processes dependant on NADP and NAD.

What is claimed is:

1. A non-human non-naturally-occurring organism transformed to express an enzyme having a sequence of greater than 70% identity to SEQ ID No. 2 and capable of transferring reducing equivalents between pyridine nucleotide cofactors.

2. The whole cell or microorganism according to claim 1, wherein said enzyme is soluble pyridine nucleotide transhydrogenase.

3. The nucleotide molecule having a sequence of greater than 70% identity to SEQ ID No.1, encoding an enzyme having the activity of soluble pyridine nucleotide transhydrogenase.

4. A process for analyzing a chemical reaction, wherein said process comprises catalyzing said chemical reaction using the whole cell or microorganism of claim 1 as a biocatalyst.

5. A process for converting a substrate to a product, said process comprising reacting said substrate with:

(a)(i) an enzyme having a sequence of greater than 70% identity to SEQ ID No. 2 and capable of transferring reducing equivalents between pyridine nucleotide cofactors; or (a)(ii) an organism as defined in claim 1; and (b) a pyridine cofactor.

6. The process according to claim 5, which is a biotransformation or assay.

7. The process according to claim 5, wherein said cofactor is used in a catalytic amount.

8. The process according to claim 5, wherein said substrate is morphine.

9. The process according to claim 6, wherein said substrate is morphine.

10. The nucleotide molecule according to claim 3, wherein said nucleotide molecule comprises the nucleotide sequence shown in SEQ ID No. 1.

11. The nucleotide molecule according to claim 3, wherein said nucleotide molecule comprises the nucleotide sequence of nucleotides 209 to 1600 shown in SEQ ID No. 1.

* * * * *

UNITED STATES PATENT AND TRADEMARK OFFICE
CERTIFICATE OF CORRECTION

PATENT NO. : 6,440,688 B1
DATED : August 27, 2002
INVENTOR(S) : Neil Charles Bruce and Christopher Edward French It is certified that error appears in the above-identified patent and that said Letters Patent is hereby corrected as shown below:

Column 13,
Line 1, "A non-human, non-naturally-occurring organism" should read -- A non-naturally-occurring whole cell or microorganism --.
Line 46, "The nucleotide" should read -- An isolated nucleotide --.
Line 50, "analyzing" should read -- catalyzing --.
Lines 55-58 through Column 14, line 38, "(a)(i) an enzyme having a sequence of greater than 70% identity to SEQ ID No. 2 and capable of transferring reducing equivalents between pyridine nucleotide cofactors; or (a)(ii) an organism as defined in claim 1; and" should read -- (a) the transformed whole cell or microorganism as defined in claim 1; and --.

Signed and Sealed this

Eleventh Day of February, 2003

JAMES E. ROGAN
*Director of the United States Patent and Trademark Office*